US010506828B2

(12) United States Patent
Dai et al.

(10) Patent No.: US 10,506,828 B2
(45) Date of Patent: Dec. 17, 2019

(54) PERSONAL VAPORIZER WITH LIQUID SUPPLY BY SUCTION

(71) Applicant: Westfield Limited (Ltd.), Hong Kong (CN)

(72) Inventors: Wei Dai, Shanghai (CN); Yongjie James Xu, Richmond, VA (US)

(73) Assignee: WESTFIELD LIMITED (LTD.), Hong Kong (CN)

( * ) Notice: Subject to any disclaimer, the term of this patent is extended or adjusted under 35 U.S.C. 154(b) by 272 days.

(21) Appl. No.: 15/277,591

(22) Filed: Sep. 27, 2016

(65) Prior Publication Data

US 2017/0013884 A1 Jan. 19, 2017

Related U.S. Application Data

(62) Division of application No. 14/231,339, filed on Mar. 31, 2014, now Pat. No. 9,642,397.

(51) Int. Cl.
| | |
|---|---|
| *A24F 47/00* | (2006.01) |
| *A61M 15/06* | (2006.01) |
| *B67D 7/02* | (2010.01) |
| *F22B 1/28* | (2006.01) |
| *H05B 1/02* | (2006.01) |

(52) U.S. Cl.
CPC ........... *A24F 47/008* (2013.01); *A61M 15/06* (2013.01); *B67D 7/0277* (2013.01); *F22B 1/284* (2013.01); *H05B 1/0297* (2013.01)

(58) Field of Classification Search
CPC .............................. A61M 15/06; A24F 47/008
See application file for complete search history.

(56) References Cited

U.S. PATENT DOCUMENTS

| | | | |
|---|---|---|---|
| 4,735,217 A | 4/1988 | Gerth et al. | |
| 4,922,901 A | 5/1990 | Brooks et al. | |
| 5,894,841 A * | 4/1999 | Voges | A24F 47/008 128/203.12 |
| 7,845,359 B2 | 12/2010 | Montaser | |
| 8,079,371 B2 | 12/2011 | Robinson et al. | |
| 8,113,390 B2 * | 2/2012 | Wold | B05B 11/025 222/389 |
| 2011/0094523 A1 * | 4/2011 | Thorens | A24F 47/008 131/194 |
| 2013/0081642 A1 * | 4/2013 | Safari | A24F 47/008 131/329 |
| 2014/0283855 A1 * | 9/2014 | Hawes | A24F 47/008 131/328 |
| 2015/0272216 A1 | 10/2015 | Dai et al. | |

OTHER PUBLICATIONS

Beyhaghi et al., Wicking and Evaporation of Liquids in Porous Wicks: A Simple Analytical Approach to Optimization of Wick Design, 2014, AICHE Journal, vol. 0 n. 5, p. 1930-1940.*

(Continued)

*Primary Examiner* — Anthony Calandra
(74) *Attorney, Agent, or Firm* — Nixon & Vanderhye P.C.

(57) ABSTRACT

A personal vaporizer having a pressure-induced liquid supply that allows a user to draw liquid from a liquid reservoir through applying a suction force on the mouthpiece. The amount of liquid drawn is proportional to the pressure induced, and proportional to the amount of vaporization a user may desire.

16 Claims, 3 Drawing Sheets

(56) References Cited

OTHER PUBLICATIONS

Vaporizer Learning Center, Vape World, http://www.vapeworld.com/learning-center, 5 pages, downloaded Nov. 8, 2013.
Vaporizer Buying Guide, Vape World, http://www.vapeworld.com/vaporizer-buying-guide, 9 pages, downloaded Nov. 8, 2013.

* cited by examiner

PERSONAL VAPORIZER WITH LIQUID SUPPLY BY SUCTION

This application is a divisional application of U.S. application Ser. No. 14/231,339 filed Mar. 31, 2014, the entire contents of which are hereby incorporated by reference.

BACKGROUND OF THE DISCLOSURE

The present disclosure generally relates to micro-vaporizers and particularly to micro-vaporizers for small handheld devices.

Vaporizers convert a liquid or solid into a vapor typically by heating to promote evaporation. Many products have micro-vaporizers that typically vaporize liquids at a rate of less than 50 milliliters per hour (ml/h). The vapor may be inhaled, dispersed in the air to create a scent, or used in some other manner. Micro-vaporizers may be used in products such as electronic cigarettes, fragrance dispensers, milliliters per hour mosquito, or other bug repellent diffusers, air and environment purification units, and essence or aromatic diffusers.

Micro-vaporizers may be used in electronic cigarettes to produce a vapor from nicotine liquid in place of the smoke created by the burning of tobacco products. As a user inhales from an electronic cigarette, a flavored, nicotine-containing liquid contained in the cigarette is heated to produce vapor. A battery in the cigarette may be used to power a heating element. The heater rapidly heats the liquid to generate the vapor that simulates smoke.

Users may prefer that their electronic cigarettes have characteristics similar to tobacco cigarettes. The size and shape of both types of cigarettes may preferably be about the same. Tobacco cigarettes generate smoke almost instantaneously when a user inhales. An electronic cigarette preferably also generates vapor almost instantaneously. Tobacco cigarettes are generally cheap and disposable; thus, cheap and disposable electronic cigarettes may also be commercially desirable.

Structurally, conventional electronic cigarettes use fiber strings to draw or direct liquid stored in a reservoir towards the surface of a heating element to vaporize the liquid. The fiber strings are directly in contact with the surface of the heating element. The conventional fiber strings may have problems in the heat transfer efficiency and fluid leakage.

In the conventional structure, liquid is directed or drawn by a fiber string that is in close or direct contact with the heating element surface. Because liquid is absorbed by the fiber strings, vaporization occurs on the surface of the fiber string. Consequently, mainly the liquid on the surface of the fiber strings is vaporized and remainder of the liquid absorbed into the fiber strings is heated but does not vaporize. Heating a liquid that do not vaporize causes excessive power usage, which may drain the battery in the cigarette.

The conventional fiber string structure tends to allow liquid to leak because the liquid continues to seep into fiber string while the cigarette is not in use. The liquid absorbed in the fiber string may leak through the open vapor channel and exit through the mouthpiece.

Further, fiber strings tend to absorb liquid in proportion to the diameter of the string. The amount of liquid adsorbed by the strings generally is more than the amount of liquid needed to convert to vapor in a volume that a user may desire during a single inhalation.

Also if a user applies a small suction force, the excessive amount of vapor in the vapor channel may condense and become a liquid form. The condensed liquid may be unable to be recaptured and vaporized, and thus leak through the mouthpiece.

Electronic cigarettes typically have a heating element that quickly heats up to generate vapor. Other types of conventional vaporizers may use a direct flame to vaporize liquid but flames may not be suitable for an electronic cigarette.

Further, a user may need to learn and become accustomed to an electronic cigarette or other type of vaporizer. The user may need to adjust to the heating time and method of each type of conventional vaporizers. For example, the conventional vaporizers that use tube delivery systems may require the users to learn the proper draw speed of the vaporizer, and the vaporizers that use flame powered units may need to learn the correct flame distance and draw.

One type of commercially desirable electronic cigarette shape may be similar to a conventional tobacco cigarette. It may be challenging to develop electronic cigarettes that have characteristics similar to tobacco cigarettes, such as the small diameter, cylindrical shape, and compact portability of a tobacco cigarette. One of the difficulties is that the desired shape and size of a conventional tobacco may not fit conventional batteries, such as an alkaline battery. The electrical energy discharge rate needed to heat and vaporize the liquid in an electronic cigarette may exceed the energy stored in low-cost conventional batteries and conventional rechargeable batteries. Batteries that store and discharge large amounts of energy, such as lithium batteries, are typically expensive, and may not be viable for a disposable electronic cigarette.

In view of these challenges and others, there continues to be a long felt and unmet need for low cost, lower energy consumption, and controllable vapor capacity micro-vaporizers for electronic cigarettes and other similar devices.

SUMMARY OF INVENTION

To efficiently vaporize liquid and prevent leakage, sufficiently high temperature may be required to be supplied to a small surface area of liquid that is proportional to a user's applied force. In particular, the most efficient process to vaporize liquid in an electronic cigarette may be to vaporize a proportionately sufficient liquid to produce a desired amount of vapor by applying liquid directly to the surface of the heating element.

An embodiment of the invention addresses the desired characteristic by providing an electronic cigarette having a mouthpiece including an opening, a vaporization chamber housing a heating element and a liquid transportation device, and a liquid storage chamber housing a liquid reservoir and an air duct that communicates between the vaporization chamber and the liquid storage chamber.

The invention further includes the vaporization chamber being adapted to have a lower pressure than the liquid storage chamber.

An embodiment of a liquid transport device in an electronic cigarette may have a support body of a liquid transport device, a cavity in the support body, and an opening in the cavity that is in close proximity to a heating element such that an amount of liquid less than a natural droplet can be supplied to the heating element.

The invention further includes a method to produce vapor in an electronic cigarette by: 1) providing a suction force to a mouthpiece of an electronic cigarette through a mouthpiece opening, 2) inducing a negative pressure in the mouthpiece, 3) drawing an amount of liquid from a liquid reservoir through an opening in a liquid transport device of the electronic cigarette due to the negative pressure induced, 3) supplying the amount of liquid drawn from the liquid reservoir onto a heating element, and 4) producing vapor using the liquid supplied to the heating element by heating the vapor on a surface of the heating element.

DETAILED DESCRIPTION OF THE INVENTION

This invention is directed to provide an efficient vaporization method that may be applied to a personal vaporizer, such as an electronic cigarette.

As a user inhales through a mouthpiece of an electronic cigarette described herein, a negative pressure is created in a vaporization chamber. The negative pressure is used to: 1) drawn fresh air into the electronic cigarette through vent holes; 2) may activate an "air-pressure sensitive" on and off flow switch; and 3) draw liquid from a reservoir onto a heating element in the electronic cigarette for immediate vaporization upon contact with a surface of the heating element. The amount of vaporization may be controlled by the user through controlling the amount of suction force applied to the electronic cigarette.

Figure 1:
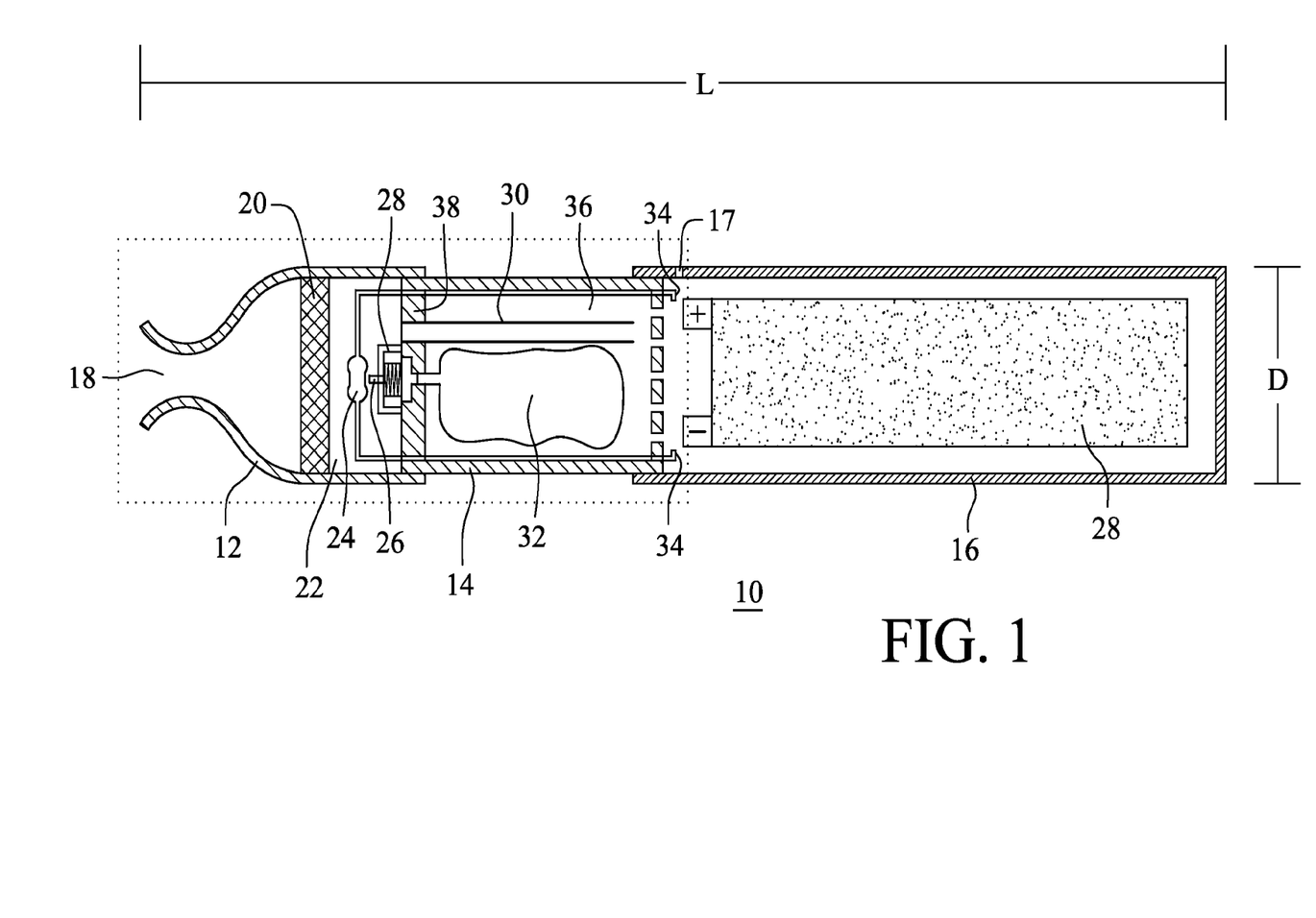
FIG. 1 is a schematic diagram showing in cross-section a first embodiment of a personal vaporizer, such as an electronic cigarette.

FIG. 1 is a schematic diagram showing in cross-section an embodiment of a personal vaporizer, such as an electronic cigarette 10. The cigarette 10 may have a generally cylindrical shape with a diameter (D) of about 10 millimeters (10 mm) and a length (L) of between 75 to 120 mm. These are the dimensions of a conventional tobacco cigarette. The dimensions may vary depending on the embodiment of the cigarette 10 and on whether the electronic cigarette 10 is to have the same dimensions of a tobacco cigarette.

In another embodiment, the personal vaporizer may not be in a cylindrical shape as shown in FIG. 1, and may be in different shapes that may be desirable to a user, and may include similar components as described herein.

The electronic cigarette 10 is one embodiment of a personal device including a micro-vaporizer. Other applicable devices may include small hand-held or pendant type dispensers for fragrance, bug repellant and other vapors or mist products. In another embodiment, the personal device may use a micro-vaporizer to deliver medicine or other therapeutic vapor or mist.

The electronic cigarette 10 may include a mouthpiece 12, a proximal cylindrical housing section 14 and a distal cylindrical housing section 16. The mouthpiece is hollow and includes a mouthpiece opening 18 that allows vapor to pass from the cigarette 10 into the mouth of a user. The mouthpiece 12 may house a mouthpiece membrane 20 that is in close proximity to the opening 18. The membrane 20 may be, e.g., a porous filter, a non-fibrous material, a woven material, a non-woven fibrous material, a highly absorbent breathable material, or any other types of material that has the ability to absorb liquid droplets in the mouthpiece or vapor condensates during the vaporization process. The membrane 20 may have the ability to absorb up to ¼ of the liquid in a liquid reservoir used in the electronic cigarette. The membrane 20 may be disc shaped, rectangular shaped, triangular shaped, or a combination of the shapes, and may entirely fill the hollow interior of a portion of the mouthpiece. The membrane 20 may catch liquids in the vapor so that liquid may not leak from the mouthpiece opening 18.

The mouthpiece 12 may also contain a vaporization chamber 22 on the opposite side of the membrane 20 from the opening 18. The vaporization chamber 22 may house a heating element 24, a liquid transport device 26 connected to a one-way valve 28, all of which may be located on and/or supported by a proximal housing support 38. The proximal housing support 38 provides a substantial divider between the mouthpiece 12 and the proximal cylindrical housing section 14.

The proximal cylindrical housing section 14 may contain a liquid storage chamber 36 that is defined by the proximal housing support 38 and a distal housing support 40. The liquid storage chamber may include at least one air duct 30 that communicates between the vapor chamber and the liquid storage chamber, and a liquid reservoir 32 that includes an opening that may be connected to and controlled by the one-way valve 28 and the liquid transport device 26. The liquid reservoir 32 may be preferably designed to contain at least enough liquid to supply vapor during at least one session.

The distal housing support 40 may be designed to have at least one opening, or other passages that allow air to pass through the support 40. These openings or passages provide fluid communication between the liquid storage chamber 36 and the distal cylindrical housing section 16. The distal cylindrical housing section 16 may include at least one vent 17 that provide an opening to the atmospheric environment. Vent 17 may supply air into the distal cylindrical housing section 16, and through the distal housing support 40 into liquid storage chamber 14.

The user inhales vapor from the cigarette 10 in a cyclical manner. During each cycle, the user may inhale for a few seconds. The amount of vapor inhaled by the user during each cycle is referred to as the "vapor volume." The heating element 24 preferably produces sufficient vapor volume to satisfy the user's desire for vapor during each cycle. The user may pause between each period of inhaling vapor. The duration of the pause may vary from very short, e.g., one or two seconds, to relatively long, e.g., ten to seconds. During each session, the user may repeat the cycle of inhaling vapor and pausing. The duration of each cycle and the number of cycles may vary. The vapor volume produced by the heating element 24 may be dependent upon the amount of liquid supplied to the heating element as induced by a user's inhalation habits, the liquid may be drawn through the liquid transport device 26 and the one-way valve 28.

In an embodiment, the one-way valve 28 may enable liquid to be drawn from the liquid reservoir 32 and pass through the proximal housing support 38 to enter the vapor chamber 22. The one-way valve 28 may not allow liquid to flow in the opposite direction and reenter the liquid reservoir 32. Liquid is drawn from the liquid reservoir 32, through the valve 28 and is applied to a surface of the heating element 24. The valve 28 is actuated, e.g., opened, by applying a suction force to the mouthpiece 18 and to induce a pressure change between the vaporization chamber 22 and the liquid storage chamber 36. When the valve 28 is open, the fluid moves from the reservoir 32, through the valve 28 and to the heating element 24 due to the pressure difference between the reservoir 32 and the heating element 24.

Figure 2:
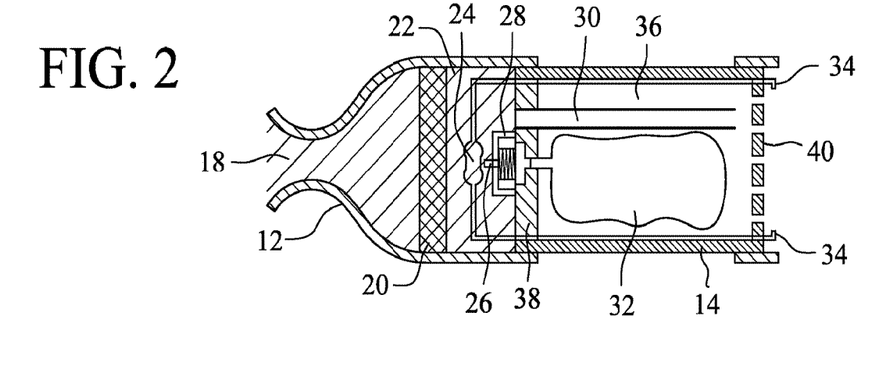
FIG. 2 is an enlarged cross-sectional view of a portion having the mouthpiece, heating element, and liquid reservoir of the electronic cigarette shown in FIG. 1.

FIG. 2 depicts pressure differences that may be induced in the mouthpiece 12 and the proximal cylindrical housing section 14. A user applies a suction force on the opening 18, and the force may induce a negative pressure in the mouthpiece 12 as compared to a positive pressure in the liquid storage chamber 16. The positive pressure zone is open to the atmosphere through vent 17 in the distal cylindrical housing section 16. The negative pressure, e.g., a pressure slightly below atmospheric pressure, may be induced in the entire mouthpiece 12 portion, including the opening 18 and the vaporization chamber 22.

When a negative pressure is induced, the negative pressure in the mouthpiece 12 would force air to be drawn from the positive pressured liquid storage chamber 32 through the air duct 30. The pressure would also force liquid to be drawn through an opening in the liquid transport device 26 and the attached one-way valve 28. Simultaneously, the force that draws air from the liquid storage chamber 36 would also induce air to be drawn from the vent 17 in the distal cylindrical housing section 16 to replace the air drawn from the liquid storage chamber 36.

The liquid drawn into the vaporization chamber 22 by the negative pressure in the mouthpiece 12 is applied to a surface of the heating element 24 and vaporized in the vaporization chamber 22. When a vapor is produced, the user then may apply more suction force and inhale the vapor. The inhalation act by the user would induce further negative pressure in the mouthpiece 12, and repeat the process of drawing liquid from the liquid reservoir 32, thus producing more vapor in the vaporization chamber 22.

However, because the mouthpiece 12 and the liquid storage chamber 22 are able to communicate through the air duct 30, the pressure difference induced is only formed for a short period of time, and then the pressure is rebalanced as air is drawn into the mouthpiece 12 from the liquid storage chamber 36 that is open to the atmosphere through the at least one opening in the distal housing support 40 and the vent 17. Thus, the amount of liquid drawn from the liquid reservoir 32 due to the decrease in pressure in the mouthpiece 12 may be minimal, and proportionate to the pressure difference.

The pressure difference induced in the mouthpiece 12 may be directly related to the suction force applied by a user on the opening 18. An increase in the suction force a user applies on the opening 18 may also increase the negative pressure induced in the mouthpiece 12. As the pressure becomes more negative in the mouthpiece 12, the pressure difference increased between the mouthpiece 12 and the liquid storage chamber 36. As the difference increases, liquid drawn from the liquid reservoir 32 also increases. Thus, more liquid would be applied to the surface of the heating element 24, and vapor produced would also increase.

The liquid reservoir 32 may be a collapsible liquid reservoir 32 and may resemble a bladder that is made of a plastic, a little or non-elastic thin film, or any type of material that is collapsible and may hold liquid or a solid tube with an inside sliding plug. The liquid reservoir 32 may be enlarged when filled with a desired liquid to be vaporized. As liquid is drawn from the reservoir, the liquid reservoir 32 may collapse and shrink. The liquid reservoir 32 may be filled with only liquid, without any gases inside the liquid reservoir 32. The pressure of the liquid in the liquid reservoir 32 may remain constant, e.g., at atmospheric pressure.

When a user induces negative pressure in the mouthpiece 12, the positive pressure in the liquid storage chamber 36 may cause the liquid reservoir 32 to collapse or shrink. The liquid reservoir 32 may be open to the environment at only the liquid transport device 26 and one-way valve 28 such that the liquid reservoir 32 may not draw air from the environment into the liquid reservoir 32. The collapsible design of the liquid reservoir 32 may enable a user to use the device and draw liquid from the liquid reservoir 32 regardless of the orientation of the device during the vaporization process.

Figure 3A:
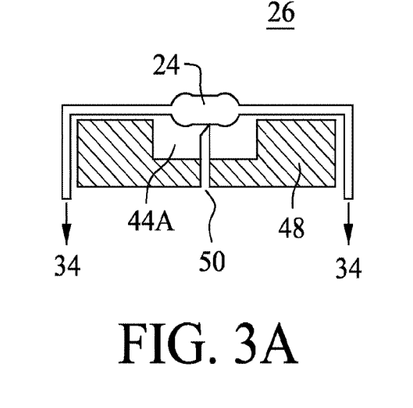
FIG. 3A is an enlarged view of a first embodiment of the heating element and liquid delivery system including a tube inside the mouthpiece shown in FIG. 1.
Figure 3B:
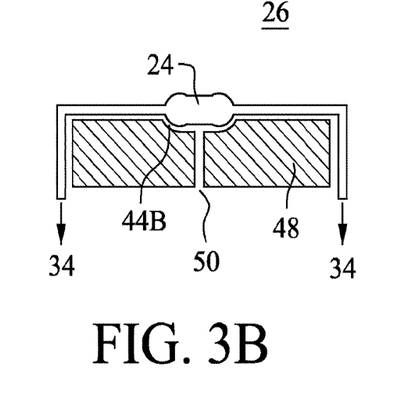
FIG. 3B is an enlarged view of a second embodiment of the heating element and liquid delivery system without a tube inside the mouthpiece shown in FIG. 1.
Figure 3C:
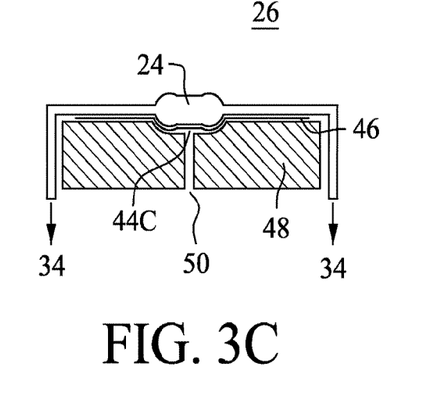
FIG. 3C is an enlarged view of a third embodiment of the heating element and liquid delivery system including a membrane layer inside the mouthpiece shown in FIG. 1.

FIGS. 3A, 3B, and 3C depict three embodiments of a liquid transport device 26 that may be used in an electronic cigarette or other type of vaporizer, such as one described above and shown in FIG. 1. The liquid transport device 26 may be designed to apply liquid onto a surface of the heating element 24 in an efficient manner that does not require the use of, or produce, excess liquid drawn from the liquid reservoir 32.

The liquid transport device 26 may also be designed to apply liquid onto the heating element 24 to allow instantaneous vaporization as the user's applies a suction force to the opening 18 by heating only an amount of liquid drawn by the suction force to create the vapor volume desired by the user. The remaining amount of liquid may be stored in the liquid reservoir 32 which is separated from the heating element 24. The liquid in the liquid reservoir 32 is not heated as the user inhales the vapor. Thus, the liquid in the reservoir 32 does not cool the heating element 24 or cause additional energy to be drawn from a power source. The liquid may only flow from the reservoir 32 to the heating element 24 as needed to create the vapor volume.

An electronic cigarette user may consume vapor at an average of a minimum amount of about 0.15-0.75 μl and a maximum about of about 15-30 μl, and have an inhalation period of between about 0.5-5.0 seconds. These values are exemplary and do not limit the scope of the invention. When a user has a short inhalation period, the vapor production desired may be relative to the inhalation period, and thus the liquid required is a small amount. The liquid desired to be vaporized at a minimum amount of vapor inhalation may be less than a natural droplet.

The liquid transport device 26 may be designed to allow efficient vaporization such that the entire amount of liquid drawn is an amount that can be instantaneously vaporized. The vaporization amount may also be controlled such that the entire vapor produced is consumed by a user during a single inhalation cycle to prevent condensation and leakage in the mouthpiece.

To draw a liquid amount that may be efficiently vaporized and produce a small amount of vapor, the liquid transport device 26 may have an opening of about 2.5 mm or less in diameter, and may be as simple as having an aperture having the size of a pin hole. The opening of the liquid transport device 26 may be close in proximity to the heating element 24. The close proximity of the liquid transport device 26 to the heating element 24 may allow liquid to be supplied regardless of the orientation of the electronic cigarette 10. The size of the opening may allow a minimum amount of liquid desired to be vaporized to be drawn from the liquid reservoir 32, allow liquid to be drawn even if the liquid amount may not be enough to form a natural droplet.

It may be desirable to draw different amounts of liquid depending on the desired vapor production capacity of the electronic cigarette 10 in addition to the user-applied force. Adjustments in vapor production capacity may be obtained by changing the size of the air duct 30 relative to the opening in the liquid transport device 26 or adjusting the spring bias of the one-way valve. For example, if the opening in the liquid transport device 26 remains constant, the larger the diameter of air duct 30, the lesser the amount of liquid may be drawn from the liquid reservoir 32. In another example, reducing the spring bias would cause the valve to open more quickly and stay open longer to allow more liquid to flow through the valve. These adjustments would be made during the design of the electronic cigarette and not during its use.

FIG. 3A depicts a liquid transport device 26 that applies liquid to a heating element 24. The liquid transport device 26 may comprise a support body 48. The liquid transport device 26 may be coupled to the liquid reservoir 32 on a first side of the proximal housing support 38, through an opening in the proximal housing support 38, liquid may be supplied to the liquid transport device 26 on a second side of the proximal housing support 38, and applied to the heating element 24. In another embodiment, the support body 48 may comprise the proximal housing support 38.

The liquid transport device 26 may be connected to a support body cavity 44A in the shape of a rectangle that is on a first side of the support body 48, and the cavity 44A may include an opening 50. The liquid transport device 26 may comprise a tube that extends through the opening 50 in the cavity 44A to deliver the liquid drawn from the liquid reservoir 32 to the heating element 24. The tube may be less than 1 mm in diameter, and may be made of a material such as a hard, stiff plastic or metal. The tube may have a slanted cut at the tip which is close, e.g., within 3 mm, to the heating element. The opening of the tube with the slant cut assists in delivering small amounts of liquid, e.g., smaller than a drop, to the surface of the heating element. The slanted cut at the end of the tube may also assist in preventing an air bubble blockage in the tube or a blockage due to liquid remaining in the tube.

FIG. 3B depicts another liquid transport device 26. The liquid transport device may be coupled to a support body cavity 44B, in a shape of a basin, on a first side of the support body 48, and the cavity 44B includes an opening that extends through the support body 48 to a second side of the support body 48. The liquid transport device may comprise of the cavity 44B and the opening 50 in the support body 48, the opening 50 being coupled to a liquid reservoir 32 on a second side of the support body 48.

The heating element 24 is in close proximity to the support body 48 such that the heating element 24 is situated within the basin of the support body cavity 44B. The liquid is drawn from the liquid reservoir 32 and enters the opening 50 of the support body 48. The liquid diffuses into the basin of the cavity 44B to distribute the liquid onto the heating element surface.

FIG. 3C depicts another liquid transport device 26. The embodiment may comprise of a basin cavity 44C that resembles the basin cavity 44B shown in FIG. 3B, and a membrane layer 46 between the cavity 44C and the heating element 24. The membrane layer 46 may cover an outer surface of the heating element in its entirety, only on the outer surface of the heating element 24 that abuts the basin cavity 44C, partially cover the heating element along the basin cavity 44C, or may cover a thin strip of a surface of the heating element 24 that is perpendicular to the opening 50 in support body 48. The membrane layer 46 may cover between about 10-100% of the outer surface of the heating element 24, and may be of a thickness of between about 0.1 mm to about 5 mm, for example.

The membrane layer 46 aids in the diffusion of the liquid along the basin cavity 44C such that the liquid is drawn through the opening and absorbed onto the membrane layer 46, and be instantaneously vaporized from the membrane by the heating element 24. The membrane layer 46 may cover a surface area of the heating element 24 sufficient to provide the liquid to the heating element needed for the desired amount of vapor generation. The membrane layer 46 may be made out of paper, cloth, fiber, lipids, or other type of absorbent coating on the surface of the heating element 24.

The support body 48 may be made out of a durable material that can endure high temperatures, such as ceramic or plastic, or any other material that is non-absorbent and can endure high temperature. The bracket 48 may also be designed to envelope the heating element 24 entirely except for an opening for vapor to escape. The bracket 48 may also be designed to cover between about 15-99% of the outer surface of the heating element 24, or between about 25-75% of an outer surface of the heating element 24.

The liquid transport device 26 may be coupled to a one-way valve 28. The one-way valve may remain closed to prevent liquid flow from the reservoir. The valve is opened when a slight pressure difference, e.g., 200 to 400 Pa or 0.03 to 0.05 psi, occurs between the reservoir and the vaporization chamber. These pressure differences correspond to the suction created when a person inhales on the mouthpiece.

In an embodiment, The one-way valve 28 may be coupled to the liquid transport device 26 to ensure that no air flow may enters the liquid reservoir 32, and no liquid flow may reenter the liquid reservoir 32 during the occurrence of any circumstances that may cause air flow to be redirected, such as if a user blows into the mouthpiece 18.

Figure 4:
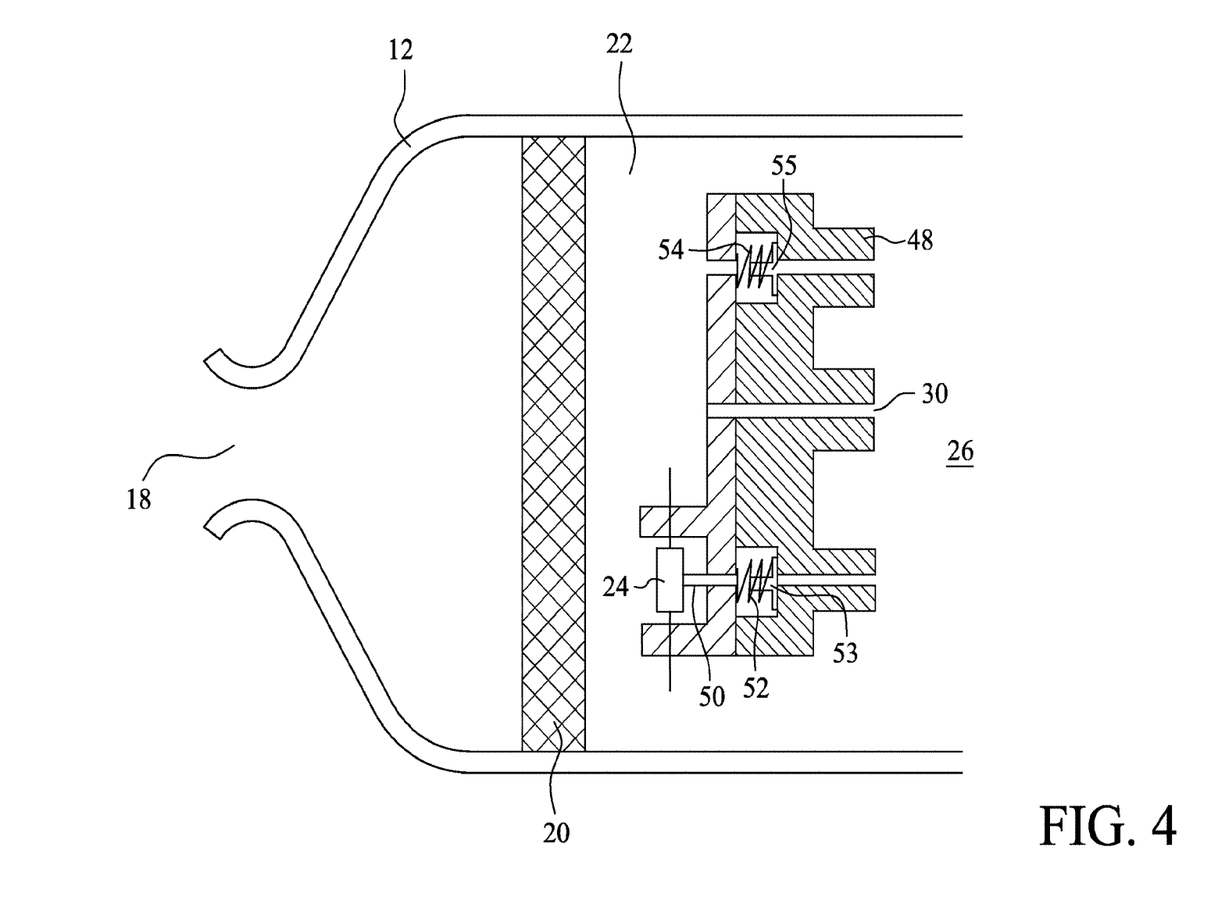
FIG. 4 is an enlarged schematic diagram of a fourth embodiment of the heating element and liquid delivery system for a larger micro-vaporizer, such as for an electronic cigar.

FIG. 4 depicts another embodiment of a liquid transport device 26 that may be used within a micro-vaporizer that operates at a larger capacity, such as an electronic cigar or the like. The liquid transport device 26 may include a support body 48, the support body 48 may enclose a first and a second cavities: the first cavity houses a plunger valve 53 that may include a spring 52, which connects to the heating element 24 via a tube 50 that extend through the support body 48 from the cavity to the heating element; and the second cavity houses a bleed valve 55 that may also include a spring 54 which activates upon an air pressure threshold increase in the liquid storage chamber to release air flow into the vaporization chamber 36. The support body 48 may also include an air duct 30 that extends between the vaporization chamber 22 and the liquid storage chamber 36.

The spring 52 may bias the plunger valve 53 against the first cavity to flow passages in the support body 48 that may be coupled to the liquid reservoir 32. The cavities in the support body 48 may be in the form of a cage for the plunger valve 53. The support body 48 may allow liquid to flow through the plunger valve 53 to flow to the heating element 24. Activation of the plunger valve may be by air pressure that is induced from a user's suction force, or through a switch that may be engaged. The force of the spring 52 may be selected such that it may be overcome by the slight pressure difference between the vaporization chamber 22 and the liquid reservoir 32 created when the user sucks on the cigarette 10. When suction is applied, the plunger valve 53 may open and liquid may flow to the vaporization chamber 22. When suction is not applied, the valve may remain closed and liquid may not flow from the liquid reservoir 32.

Air duct 30 supplies air to the vaporization chamber that is mixed with vapor and inhaled by the user. The air duct is sized to allow sufficient air needed to be inhaled and create the needed reduced pressure condition in the vaporization chamber to actuate the one way valve. The air duct 30 may have a throat diameter, e.g., the minimum diameter in the duct, of no greater than the diameter of the throat opening 31 of the mouthpiece. For example, if the mouth piece has a throat diameter of 3 mm the throat diameter of the air duct 30 would be 3 mm or less, such as 1 mm.

A bleed valve 55 may aid in the process of ensuring that air pressure in the electronic cigarette remains stable. When a user's applied suction force exceeds the maximum air intake threshold, the bleed valve 55 may open and divert airflow to allow a greater air flow into the vaporization chamber. A bleed valve 55 may be used in an electronic cigar which tend to have a larger throat diameter for the mouthpiece than do electronic cigarettes. The bleed valve 55 avoids the user having a feeling that insufficient air and vapor are flowing through the mouthpiece.

The combined use of the plunger valve 53 and bleed valve 55 may aid in the control of liquid flow from the liquid reservoir 32 to the heating element 24 such that vaporization occurs at an efficient rate as desired and controlled by the user. The temperature of the heating element 24 may be adjusted by changing the output of the heating element 24, such as changing in voltage or resistance of the heating element, changing the electrical impedance, or changing the amount of current used in the electronic cigarette 10.

Control may be adjusted such that full vaporization may be achieved even during the maximized condition, and retain the ability for a user to control the amount of fluid vaporization and condensation. Efficiency in vaporization may allow use of a minimal amount of power required to vaporize desired liquid, and improve the portability of an electronic cigarette by decreasing the need for a large housing to hold power supply, such as a battery.

Relating back to FIG. 1, a power source, such as a battery 28, may be housed in the distal cylindrical housing 16. proximal cylindrical housing section 14 may connect to, or may be integral with, the distal cylindrical housing section 16. The connection may be formed by opposing ends of the housing sections 14 and 16 engaging each other, such as by sliding one onto the other. The battery 28 in the distal cylindrical housing section 16 may provide electrical energy or power to the heating element 24. In an embodiment, the distal cylindrical housing section 16 may also include an illuminating end, e.g., a light emitting diode, to simulate a lit end of a tobacco cigarette.

One approach to minimizing the requirement for stored energy is to reduce the power needed to vaporize the liquid. The power is used by the heating element to create heat that vaporizes the liquid. The liquid cools the heating element. Power from the battery is required to overcome the cooling by the liquid and heat the temperature to a needed to create vapor. The more liquid on or near the heating element, the greater the cooling of the heating element. By reducing the amount of liquid applied onto or near the heating element, the amount of power needed to vaporize the liquid may be reduced. The power consumption of the cigarette may be reduced by heating only a sufficient amount of liquid to create the desired vapor volume. Thus, portability of an electronic cigarette 10 may be dependent upon the efficiency in liquid flow supply by the liquid transport device 26 as described in FIGS. 3A, 3B, 3C, and 4 above, to the heating element 24.

The heating element 24 may be formed with conductors that extend from the vaporization chamber 22, through the proximal housing support 38 and the liquid storage chamber 36, and the ends of the conductors extend into the distal cylindrical housing section 16.

In an embodiment, the user of the cigarette 10 may apply a suction force on the mouthpiece opening 18. The suction applied to the mouthpiece opening 18 of the cigarette 10 may create a slight reduced pressure in the cigarette 10. The difference in pressure may be detected by a pressure sensor, and the pressure sensor may activate the heating element 24. In one embodiment, the sensor may also activate a light emitting diode (LED) at the distal end of the cigarette to show that the electronic cigarette 10 is in use.

The activated heating element 24 may heat the liquid to create vapor. The heating element 24 may continue to heat the liquid and generate vapor until deactivated, e.g., turned-off. The heating element 24 may be turned off when the pressure sensor detects a pressure rise, such as when the user stops applying suction to the cigarette 10.

In another embodiment, the user may engage a switch in the cigarette 10 that may activate the electrical energy supply to the heating element 24 and produce the temperature desired for vaporization.

The stored energy tends to be a limiting design parameter in micro-vaporizer. A battery is a typical energy storage device. Batteries may be inexpensive, provide long term energy storage, portable, be small in size and provide immediate electrical power. These characteristics are generally beneficial for electronic cigarettes and other types of personal vaporizers. The batteries may be rechargeable or non-rechargeable. If rechargeable, a battery charging holder may be provided to store the cigarette. If the battery is replaceable, the housing for the battery may be removable from the proximal portion of the cigarette.

Minimizing the amount of stored energy needed in a micro-vaporizer can assist in reducing the cost of energy, reducing the size of the cigarette, extending the period of cigarette operation, and reducing the period between when suction is applied to the cigarette and vapor is inhaled.

Small cylindrical batteries, such as AAA batteries, are in widespread use and provide an inexpensive source of electrical energy for an electronic cigarette. AAA batteries have a diameter similar to the diameter of a conventional tobacco cigarette. An electronic cigarette with a single AAA battery may have a diameter, length and size similar to a conventional tobacco cigarette. Alkaline AAA batteries are inexpensive and are cheaper than lithium AAA batteries. Rechargeable AAA batteries are also widely available. Accordingly, AAA batteries, especially alkaline batteries, may be suitable for electronic cigarettes and other micro-vaporizers.

A potential short-coming of AAA batteries and other similarly small batteries is their relatively slow energy discharge capacity. The stored energy in the cigarette should be sufficient to power the heating element during an entire smoking session. The amount of energy stored and required energy discharge rate in a conventional alkaline AAA battery may be insufficient to power a cigarette during an entire smoking session. While a lithium AAA battery may provide sufficient energy for a smoking session, these types of batteries are expensive particularly for disposable cigarettes.

By controlling the amount of liquid applied to a heating element, adjusting the heating element temperature production accordingly, and vaporizing the liquid at an efficient manner, the invention may reduce the energy required in the vaporization process to enable the use of a simple and inexpensive conventional battery in an electronic cigarette.

Advantages of the embodiment designs may include: improving thermal efficiency in vaporizing liquid and producing an adequate amount of desired vapor that does not produce condensation; providing a user the ability to control the amount of vapor desired to be produced; preventing vapor condensation due to excess vapor produced; preventing fluid leakage due to vibrations on the device or environmental changes, such as temperature changes, that may cause an in-balance in pressure in the liquid reservoir of a device; ability for the device to be used in any orientation and still be able to provide adequate fluid supply to the heating element; and providing a simple structure that may be made close to or approximately the size of a conventional tobacco cigarette if desired.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method to produce vapor in a personal vaporizer, the steps comprising:
   providing a suction force to a mouthpiece of a personal vaporizer through a mouthpiece opening;
   inducing a negative pressure in the mouthpiece and a vaporization chamber open to the mouthpiece, wherein the negative pressure is lower than an atmospheric pressure around the personal vaporizer;
   drawing, due to the negative pressure in the vaporization chamber, an amount of liquid into the vaporization chamber through an opening in a liquid reservoir, wherein a deformable outer surface of the liquid reservoir deformed due to a pressure difference between the atmospheric pressure applied to the outer surface and the negative pressure applied to the liquid in the liquid reservoir, and wherein the amount of liquid drawn from the liquid reservoir is directly related to the negative pressure induced in the mouthpiece;
   supplying the amount of liquid drawn from the liquid reservoir onto a surface of a heating element in the vaporization chamber;
   vaporizing the liquid on the surface of the heating element by heating the heating element, and
   drawing the vaporized liquid from the vaporization chamber into the mouthpiece due to the suction.

2. The method to produce vapor of claim 1, wherein the liquid transport device is a cavity with an opening in the wall which is a support structure within the personal vaporizer, wherein the cavity and the opening are configured to allow liquid communication between the liquid reservoir and the mouthpiece portion.

3. The method to produce vapor of claim 2, wherein the opening of the liquid transport device is 2.5 mm or less in diameter, and the opening is in close proximity to the heating element.

4. The method to produce vapor of claim 1, wherein the liquid transport device is a tube that extends through the opening, a first end of the tube is in close proximity to the heating element and a second end of the tube is in close proximity to the liquid reservoir, and the tube is less than 1 mm in diameter.

5. The method to produce vapor of claim 1, wherein the liquid transport device includes a membrane that absorbs the amount of liquid drawn from the liquid reservoir, and the membrane is in close proximity to the heating element.

6. The method to produce vapor of claim 1, wherein the liquid is applied to the heating element in the personal vaporizer directly from the liquid transport device.

7. A method to draw liquid from a liquid reservoir of a personal vaporizer, the steps comprising:
   applying suction to a mouthpiece portion and a vaporization chamber of the personal vaporizer, the vaporization chamber is coupled to a liquid reservoir via a liquid transport device, wherein, prior to the application of the suction, an initial air pressure in the mouthpiece portion, the vaporization chamber and a liquid pressure in the liquid reservoir are in balance at atmospheric pressure;
   by applying the suction, inducing a negative pressure in the mouthpiece portion and the vaporization chamber as compared to the atmospheric pressure;
   deforming the liquid reservoir due to the suction applied to the liquid in the liquid reservoir via the vaporization chamber which reduces pressure within the liquid reservoir as compared to the atmospheric pressure applied to externally to the liquid reservoir;
   drawing an amount of a liquid from the liquid reservoir through the liquid transport device and into the vaporization chamber due to the suction and the deformation of the liquid reservoir, wherein the amount of liquid drawn from the liquid reservoir is directly related to the negative pressure induced in the mouthpiece;
   ceasing the application of the suction which reduces the differences in the negative pressure in the vaporization chamber and the atmospheric pressure of the liquid in the liquid reservoir; and
   wherein the drawing of the liquid from the liquid reservoir stops in response to the differences becoming nominal between in the negative pressure and the atmospheric pressure.

8. The method to draw liquid of claim 7, wherein the suction is applied by an inhalation action by a user.

9. The method to draw liquid of claim 7, wherein the initial air pressure in the mouthpiece is atmospheric pressure.

10. The method to draw liquid of claim 7, wherein the initial liquid pressure is a pressure caused by a density of a predetermined type of liquid in the liquid reservoir, and an air pressure that is induced in a storage chamber that houses the liquid reservoir.

11. The method to draw liquid of claim 7, wherein the liquid transport device includes a one-way valve.

12. The method to draw liquid of claim 7, wherein the liquid is applied to a heating element in the personal vaporizer directly from the liquid transport device.

13. The method to draw liquid of claim 10, wherein the balancing of the negative pressure in the mouthpiece portion and positive pressure in the liquid reservoir is caused by an inflow of air that is drawn concurrently with the drawing of the liquid.

14. A method to supply liquid to a heating element in a personal vaporizer, the steps comprising:
   drawing fresh air into the vaporizer via an opening in a mouthpiece of the vaporizer by suction;
   inducing a negative pressure in the mouthpiece and a vaporization chamber connected to the mouthpiece, wherein the negative pressure is as compared to atmospheric pressure surrounding the personal vaporizer, and wherein the vaporization chamber is connected to a liquid reservoir by an opening in the liquid reservoir;

maintaining a deformable outer surface of the liquid reservoir at atmospheric pressure;

triggering a switch in the personal vaporizer using the negative pressure, the switch is air-pressure sensitive and is configured to activate the vaporizer;

drawing an amount of liquid into the vaporization chamber from the liquid reservoir that is proportional to the negative pressure due to the negative pressure being applied via the opening to the liquid in the reservoir which reduces the pressure in the liquid reservoir and causes deformation the deformable outer surface of the liquid reservoir; and supplying the amount of liquid onto a heating element in the vaporizer.

15. The method to supply liquid of claim 14, wherein the mouthpiece is configured to allow drawing of fresh air into the vaporizer by inhalation.

16. The method to supply liquid of claim 14, wherein liquid is drawn through a liquid transport device that is configured to allow liquid communication between the mouthpiece and the liquid reservoir, and the liquid transport device is in close proximity to the heating element.

* * * * *